United States Patent [19]

Nakajima

[11] Patent Number: 4,854,301
[45] Date of Patent: Aug. 8, 1989

[54] ENDOSCOPE APPARATUS HAVING A CHAIR WITH A SWITCH

[75] Inventor: Shigeru Nakajima, Fuchu, Japan

[73] Assignee: Olympus Optical Co., Ltd., Tokyo, Japan

[21] Appl. No.: 119,742

[22] Filed: Nov. 12, 1987

[30] Foreign Application Priority Data

Nov. 13, 1986 [JP] Japan ................................ 61-270637
Feb. 6, 1987 [JP] Japan ................................ 62-025943

[51] Int. Cl.⁴ ............................................. A61B 1/04
[52] U.S. Cl. ..................................... 128/4; 297/188; 297/217
[58] Field of Search ............... 128/4, 6, 377; 297/191, 297/192, 217, 188; 433/33

[56] References Cited

U.S. PATENT DOCUMENTS

| | | | |
|---|---|---|---|
| 2,449,385 | 9/1948 | Johnson et al. | 433/33 |
| 2,620,863 | 12/1952 | Cooper | 433/33 X |
| 3,386,766 | 6/1968 | Gorelick | 297/192 |
| 4,601,284 | 7/1986 | Arakawa et al. | 128/6 |

FOREIGN PATENT DOCUMENTS 53-39834  9/1978 Japan.
55-138436 10/1980 Japan.

Primary Examiner—William H. Grieb
Attorney, Agent, or Firm—Armstrong, Nikaido, Marmelstein, Kubovcik & Murray

[57] ABSTRACT

An endoscope chair apparatus whereby the operator can inspect and treat the patient by using an endoscope while sitting on the chair and an operating switch for the endoscope apparatus is provided in a position in which the switch can be operated by the operator in this state.

12 Claims, 17 Drawing Sheets

ENDOSCOPE APPARATUS HAVING A CHAIR WITH A SWITCH

BACKGROUND OF THE INVENTION

1. Field of the Invention:

This invention relates to an endoscope chair to be used by an operator while using a medical endoscopes.

2. Related Art Statement:

Recently, there is entensively used an endoscope whereby a body cavity interior can be observed by inserting an elongated insertable part into the body cavity without requiring to incise the body cavity or a curing treatment can be made using a treating tool inserted through a forceps channel provided in the insertable part.

There has been heretofore extensively used an endoscope of a type wherein an image within a body cavity is transmitted to an eyepiece part by using a fiber bundle relay lens system to observe the interior of the body cavity or of a type wherein an image is converted to an electric video signal which is then displayed in a monitor. An operating part is provided in such endoscope so as to be gripped by the hand of the operator. As shown in the gazette of Japanese Patent Laid Open No. 13436/1980, a still camera or video camera is fitted to an eyepiece part provided in the above mentioned operating part to image the interior of a body cavity. Thus, in the case of using an endoscope, it is necessary to operate not only the endoscope but also such various apparatus around the endoscope as a still camera, video camera, forceps and endoscope light and current source apparatus. Therefore, for example, a foot switch has been provided separately from the endoscope operating part so as to help the manual operation. Such foot switch has been merely arranged on a floor so as to be operated by the foot while the endoscope user is standing.

Switches of such peripheral apparatus of an endoscope as current and light source apparatus and a video processor have been provided mostly on operating panels of the peripheral apparatus set in immovable positions.

Thus, for example, a foot switch for improving the operability is provided for an endoscope besides various switches provided in the endoscope body. However, such foot switch is to be used as merely placed on a floor, is therefore in the way of feet of the user moving frequently during the diagnosis and curing treatment and has a danger of accidentally causing a misoperation. As the various peripheral apparatus are set in immovable positions separately from the above mentioned endoscope body, the user must go to the peripheral apparatus whenever he operates the endoscope.

Further, the user performs a diagnosis or curing treatment while keeping the observing position of the endoscope and is therefore likely to be fatigued. It is desirable that the user works while sitting on a chair. However, as described above, the work is so complicated by the operation of various switches that the fatigue at the time of using the endoscope can not be reduced by sitting on a chair.

On the other hand, the operator must perform various operations while holding the operating part of the endoscope as mentioned above, the endoscope is used over a long time and therefore it is desirable to reduce the burden on the operator of holding the endoscope during the operation.

Now, a hanger for keeping not only an endoscope but also treating tools has been often used but is not to be used while the endoscope is being used and is so formed as to keep the endoscope. With such hanger to be used to keep an endoscope, such large movements required in the endoscope inspection as varying in the vertical and horizontal directions the position relation between the operating part and the mouth of the patient, swinging the operating part largely rightward and leftward to be in the form of a fan and twisting the operating part to twist the insertable part can not be given to the operating part. Therefore, such hanger is not adapted for use as a holding device while the endoscope is being used.

By the way, the present applicant has suggested an article supporting apparatus by using an oil pressure in the gazettes of Japanese Utility Model Publications Nos. 39834/1978 and 25038/1980. As oil pressure is utilized therein, the apparatus is bulky.

OBJECTS AND SUMMARY OF THE INVENTION

An object of the present invention is to provide an endoscope chair apparatus whereby the operator can operate an endoscope and switch the peripheral apparatus of the endoscope while sitting on a chair so that the fatigue of the operator may be reduced and the operation of the above mentioned endoscope and switching of the peripheral apparatus for the endoscope may be easy.

Another object of the present invention is to provide an endoscope chair apparatus whereby the operator of an endoscope is relieved of gripping the operating part of the endoscope so that the fatigue of the operator may be reduced and the operator may engage exclusively in various operations and treatments.

In the endoscope chair apparatus of the present invention, a chair is provided so that, while sitting on the chair, the user of an endoscope may diagnose or treat a patient by inserting the endoscope into the body cavity of the patient and various switches and the like may be arranged on the chair.

Also, in the endoscope chair apparatus of the present invention, the above mentioned chair is provided with an endoscope holding apparatus which can be held by the operator without gripping the operating part of the endoscope.

Other features and advantages of the present invention will become apparent enough with the following explanation.

BRIEF DESCRIPTION OF THE DRAWINGS

FIG. 1 is a perspective view showing the first embodiment.

FIG. 2 is a perspective view showing the second embodiment.

FIG. 3 is a perspective view showing the third embodiment.

FIG. 4 is a perspective view showing the fourth embodiment.

FIG. 5 is a perspective view showing the fifth embodiment.

FIG. 6 is a perspective view showing the sixth embodiment.

FIG. 7 is a perspective view showing the seventh embodiment.

FIG. 8 is a schematic perspective view showing an endoscope holding apparatus of the eighth embodiment.

FIG. 9 is a perspective view showing a holding part holding an endoscope.

FIG. 10 is a sectioned view showing an attachment fitted to an endoscope.

FIG. 11 is an explanatory view showing a rotation regulating mechanism formed in the holding part.

Figure 1:
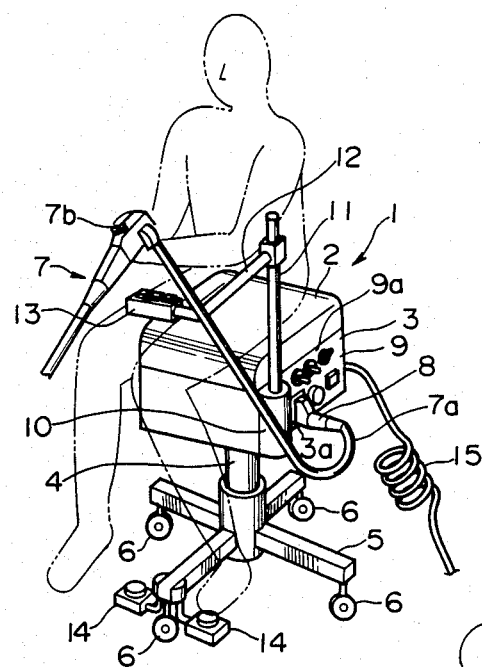
FIGS. 1 to 7 show respective embodiments of the present invention wherein an auxiliary apparatus is made as a chair apparatus.

DETAILED DESCRIPTION OF THE PREFERRED EMBODIMENTS:

Shown in FIG. 1 is the first embodiment of this invention. In the drawing, the reference numeral 1 represents a body of a chair for an endoscope operator. Below a seat part 2 in this body are provided a later described electric light source 3, a supporting pillar 4 fixed below and supporting seat part 2 and electric light source 3, and a base 5 supporting pillar 4 movably with respect to a floor. A plurality of casters 6 are provided below the base 5.

A connector 8 provided at the end of a universal cord 7a of an endoscope 7 is connected to the electric light source 3 as a body of the above mentioned endoscope apparatus so as to transmit an illuminating light and exchange information. An operating panel 9 is provided on one side of the electric light source 3 on which the connecting part 3a of this connector 8 is provided. A switch 9a for operating the electric light source 3 is provided on this operating panel 9.

A supporting part 10 projecting in the width direction of the above mentioned chair body 1 is provided in the front part of this operating panel 9a. A supporting pillar 11 is supported on this supporting part 10. At an intermediate part of this supporting pillar 11, an L-shaped bent arm 12 is fixed at the end so as to be rotatable in the peripheral direction and slidable in the vertical or axial direction of the supporting pillar 11. A switch box 13 is provided at the tip of this arm 12.

Also, foot switches 14 are provided on the above mentioned base 5 so as to be positioned below the feet of the user. The foot switches 14 are thus provided with respect to the body 1 of the chair for the endoscope operator, therefore can be prevented from being in the way below the feet when the user or the like walks and moves and can reduce the danger of misoperation.

The respective switches are positioned by considering their operating frequency. That is to say, the operating switches provided on the above mentioned operating panel 9 are so low in the using frequency as to be set only once and are, for example, a main switch and switches for switching on compressed air or an emergency light. Switches comparatively high in using frequency are provided on the above mentioned switch box 13 and are, for example, switches for adjusting the light amount and automatically adjusting the light.

Further, the above mentioned foot switches 14 are provided with switches high in using frequency the same as in the above mentioned switch box 13 and with such trigger switches required to be operated while operating the endoscope with both hands as, for example, release switches in the imaging apparatus and recording apparatus. Additional switches high in the operating frequency are provided in the operating part 7b of the endoscope 7. If the endoscope 7 is in the operating state or both hands are being used for other operations, the operation can be made easy by simultaneously using both switches. Even if the user moves while sitting on this endoscope apparatus chair, the respective switches which are provided on the body 1 of this chair will be always in the same positions with respect to the user and will be able to improve the operability to be higher than in the conventional structure. Further, as the user can operate the endoscope while sitting on the seat part 2, the fatigue in operating the endoscope can be reduced to be remarkably lower than before.

An input and output cord 15 is formed of a curled cord and therefore can be used for such signal cable as for the current source supply and other peripheral apparatus. When the above mentioned seat body 1 is moved, the cord 15 formed of a curled cord will not be in the way.

By the way, the above mentioned endoscope apparatus body may be one in which the electric light source 3 is part of a video processor used in an electronic endoscope having a built-in solid state imaging apparatus. In such case, a freeze switch is added to the release switch of the above mentioned imaging apparatus or recording apparatus.

The second embodiment shall be explained in the following with reference to FIG. 2. The fundamental structure is substantially the same as in the first embodiment and therefore the same component parts shall bear the same reference numerals to avoid duplication of the explanation.

In the drawing, the reference numeral 1 represents a body of an endoscope apparatus chair. A laser cauterizing apparatus 16 is provided as part of the endoscope apparatus just below the seat part 2 of this body 1.

A laser probe 17 inserted through a forceps channel (not illustrated) of the endoscope 7 is connected to this laser cauterizing apparatus 16. A trigger switch of this laser cauterizing apparatus 16 is the foot switch 14 removably provided on the base 5. Other respective switches are provided on a laser cauterizing panel 18 of the laser cauterizing apparatus 16. An input and output cord 19 serving as a current source supplying and earthing cord is connected to the above mentioned laser cauterizing apparatus 16.

The above mentioned foot switch 14 and laser cauterizing apparatus 16 are connected with each other through a connecting cord 20. As the above mentioned foot switch 14 can be removed from the base 5, even in case the user operates the laser cauterizing apparatus 16, for example, while standing away from the body 1 of the endoscope apparatus chair, it will be easy to arrange the above mentioned foot switch 14 below the foot of the user.

By the way, the laser cauterizing apparatus 16 serving as part of the body of the above mentioned endoscope apparatus may be a high frequency current source. In such case, the above mentioned laser probe 17 is made with a high frequency trap. A holder (not illustrated) supporting the operating part 7b or the vicinity of the operating part 7b of the endoscope 7 may be provided on the body 1. Further, the above mentioned seat part 2 may be of a material having high friction or may be of a structure provided with concavo-convexes or the like so as to be hard to slip.

The third embodiment of the present invention shall be explained in the following with reference to FIG. 3. The same component parts as in the above mentioned respective embodiments bear the same reference numerals to avoid need for explanation.

In the drawing, the reference numeral 1 represents a body of an endoscope apparatus chair. A control box 21 of the endoscope apparatus is provided below the seat part 2 of the body 1. This control box 21 is provided with switches 21a of the endoscope apparatus. Here, the above mentioned seat part 2 is respect to the base 5. An input cord 22 and output cord 23 are connected to the above mentioned control box 21. These input cord 22 and output cord 23 are connected respectively to peripheral apparatus 24 and 25.

A foot switch 14 is provided on the base 5 and is connected to the above mentioned control box 21 through a connecting cord 26.

The above mentioned seat part 2 is provided in the seating part with such recess 27 as is shown in the drawing so that the user may easily positively control the rotation and movement of the seat part while being seated.

As shown in the drawing, if the user is to rotate the endoscope 7, for example, in the direction of arrow A to change the visual field direction of the endoscope 7, the user will twist his body but, as the above mentioned seat part 2 is rotatable with respect to the base 5, he will be able to easily twist the body.

Further, a locking mechanism (not illustrated) locking together the above mentioned seat part and base 5 is provided on them so that the entire body 1 may be rotated on the floor through castors 6.

With such formation, if the chair is used without being moved, only the seat part 2 will be able to be rotated and therefore the operability will be improved.

Figure 4:
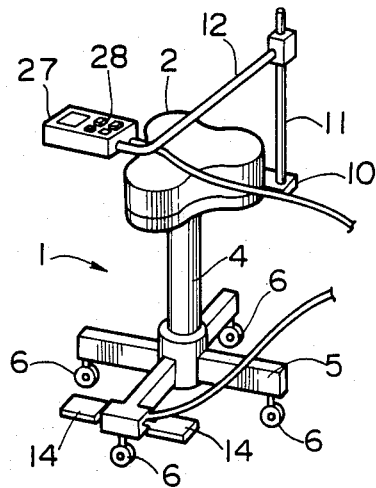

The fourth endoscope of the present invention shall be explained in the following with reference to FIG. 4. The same component parts as in the above mentioned respective embodiments bear the same reference numerals to avoid need for explanation.

In the drawing, the reference numeral 1 represents a body of a chair for an endoscope apparatus. A seat part 2 of this body 1 is rotatably supported by a supporting pillar 4 which is supported by a base 5 having castors 6 in the lower part. The above mentioned seat part 2 is formed to be substantially bicycle saddle-like so that the operator may be seated with both legs in contact on the sides with the seat part 2 and therefore the rotation may be easily controlled. A supporting part 10 is provided on one side of the above mentioned seat part 2. A supporting pillar 11 is provided on this supporting part 2. An arm 12 bent to be L-shaped, for example, in the horizontal direction is fixed at the end to an intermediate part of this supporting pillar 11 so as to be rotatable in the peripheral direction and slidable in the axial direction of the above mentioned supporting pillar 11. A displaying panel 27 is provided at the tip of the above mentioned arm 12. For example, a switch 28, monitor screen and displaying part of the endoscope apparatus (not illustrated) are provided on this displaying panel 27. Foot switches 14 are provided on the above mentioned base 5 so as to operate the endoscope apparatus not illustrated.

Figure 5:
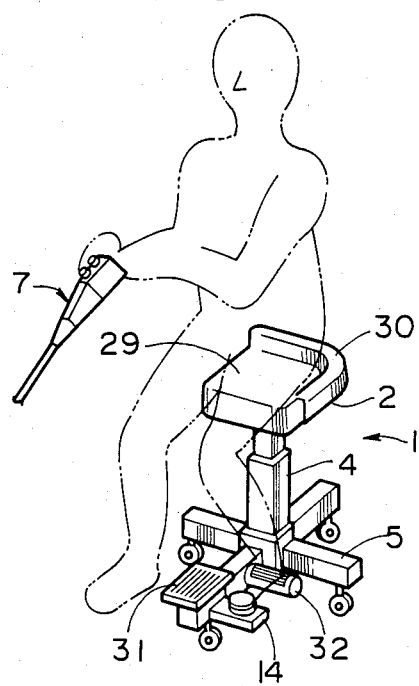

The fifth embodiment of the present invention shall be explained in the following with reference to FIG. 5. The same component parts as in the above mentioned respective embodiments bear the same reference numerals to avoid explanation.

In the drawing, the reference numeral 2 represents a seat part provided on a body 1 of a chair for an endoscope apparatus. This seat part 2 is supported by a retractable supporting pillar 4, for example, in a rectangular form so as to be adjustable in conformity with the length of the legs of the user and the height of a bed (not illustrated).

The above mentioned seat part 2 is formed to be of such area of 300 to 1000 cm$^2$ as can seat about half of the hip. A recess 29 is provided on the seating part of this seat part 2 and a frame-like projection 30 is provided outside the seating part. The stability when the operator is seated on the seat is improved by the recess 29 and projection 30.

A plate-like foot resting part 31 is provided at the outside tip on the base 5. A frictional area is made on the upper surface of this foot resting part 31 and can be used also to pull the body 1 while operating the endoscope 7.

A columnar foot supporting part 32 is provided near the supporting pillar 4 of the above mentioned base 5. A foot switch 14 is provided on the tip of the base 5. In the case of operating this foot switch 14, the heel may be supported on the above mentioned foot supporting part 32 and the foot switch 14 may be operated with the toe. While preparing for the operation, the foot may be kept supported on the foot supporting part 32. While moving, the heel can be always kept in the position in which the toe reaches the foot switch 14.

With such an arrangement, if the operator must diagnose many patients and move frequently as, for example, in the case of group diagnoses of stomachs and in an operation requiring a long time as, for example, in color endscope inspection, the seating for a short time is so easy that the fatigue degree can be reduced to be lower than before.

The body 1 is formed to be so small as to be able to be pulled with one foot and therefore the operator can be seated without influencing the operation of the endoscope inserted into the patient.

Further, even while the operator sits down, the leg not seated is free and therefore the body 1 can be easily positively moved and rotated.

By the way, in case the recess 29 and projection 30 need not be provided on the above mentioned seat part, the seat part 2 and foot resting part 31 may be rotatably provided with each other.

Figure 6:
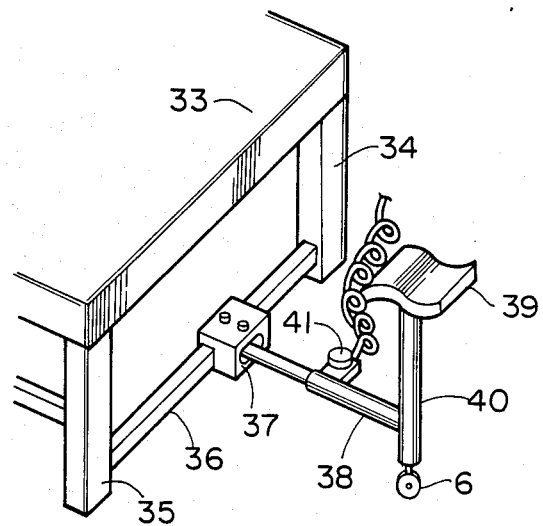

The sixth embodiment of the present invention shall be explained in the following with reference to FIG. 6.

In the drawing, the reference numeral 33 represents a bed to be used by the patient at the time of the diagnosis and curing treatment. A rail 36 is fixed at both ends between legs 34 and 35 provided on one side of this bed 33.

A sliding supporting part 37 sliding along this rail 36 is provided part of this rail 36. A retractable arm 38 is pivoted at one end to this sliding supporting part 37 so as to be rotatable by a fixed angle. A supporting pillar 40 having a seat part 39 rotatably provided in the upper part is fixed to the other end of this arm 38, is retractable in the vertical direction and is provided with a castor 6 at the lower end. Locking mechanisms not illustrated are provided respectively in the retracting part and rotating part.

Further, a foot switch 41 such as switch of the endoscope apparatus is provided on a part of the above mentioned arm 38.

Thus, the sliding part and rotating part are provided for the chair provided for the bed 33 and are further provided respectively with locking mechanisms so that the user may freely select the moving direction and may fix the chair in any position.

By the way, the above mentioned locking mechanism may be electrically remote-controlled.

Figure 7:
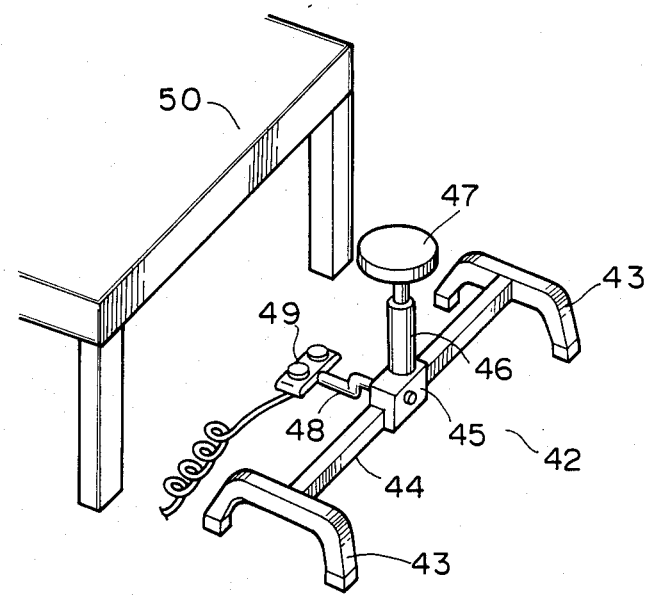

The seventh embodiment of the present invention shall be explained in the following with reference to FIG. 7.

In the drawing, the reference numeral 42 represents a body of a chair for an endoscope apparatus. This body 42 is provided with legs 43 bent to be substantially channel-shaped. A rail 44 is fixed at both ends to these legs 43 and is provided in part with a sliding supporting part 45 slidable along this rail. This sliding supporting part 45 is provided with a vertically retractable supporting pillar 46. A rotatable seat part 47 is provided at the upper end of this supporting pillar 46.

An arm 48 is fixed at one end to the above mentioned sliding supporting part 45 and is provided at the other end with a foot switch 49 serving as a switch of the endoscope apparatus. In the drawing, the reference numeral 50 represents a bed to be used by the patient.

With such formation, there can be provided an endoscope apparatus chair which has less freedom than in the sixth embodiment but has no obstacle below the feet.

Figure 8:
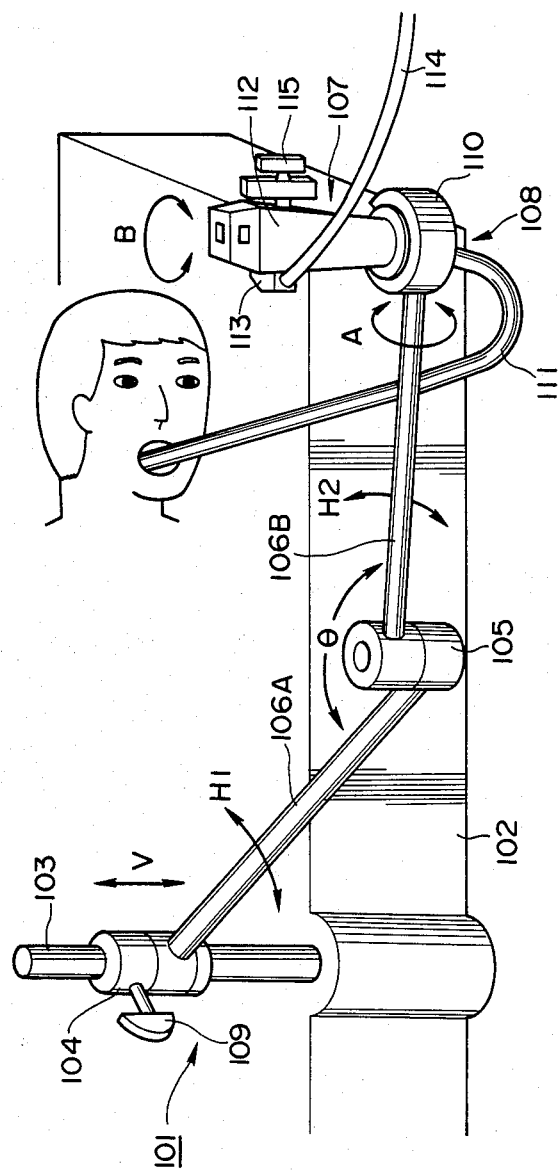
FIGS. 8 to 11 relate to the eighth embodiment of the present invention.
Figure 9:
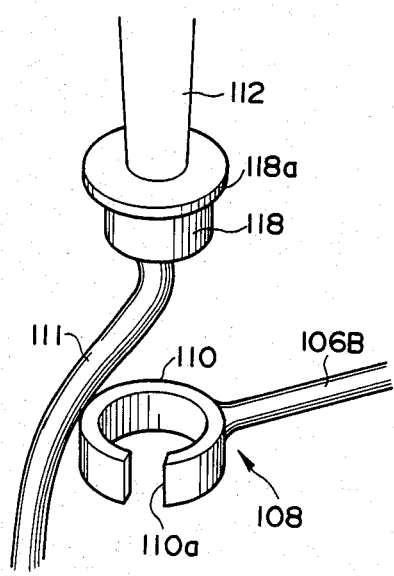
Figure 10:
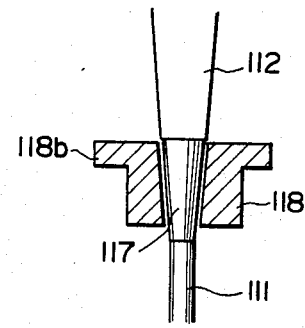
Figure 11:
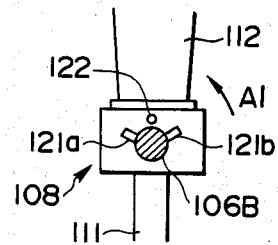

FIGS. 8 to 11 relate to the eighth embodiment of the present invention. FIG. 8 shows an endoscope holding apparatus of the eighth embodiment. FIG. 9 is a perspective view showing a holding part for holding an endoscope. FIG. 10 is a sectioned view showing an attachment fitted to the endoscope. FIG. 11 is an explanatory view showing a rotation regulating mechanism formed on the holding part.

As shown in FIG. 8, an endoscope holding apparatus 101 is formed of a supporting pillar 103 erected on a bed 102, a pair of arms 106A and 106B extending in the horizontal direction through an arm receiver 104 which can be fixed to supporting pillar 103 variably in the height and rotatably pivoted with respect to each other by an articulation 105 between the arms, and a holding part 108 holding an endoscope 107 fitted to the end of arm 106B.

The above mentioned arm receiver 104 is substantially cylindrical ring-like, can freely slide and move in the height direction (vertical direction) as shown by the arrow V as fitted to the outer periphery of the supporting pillar 103 and can be fixed with a fixing screw 109 in any height position. When this arm receiver 104 to which arm 106A is secured in the base part is rotated with the fixing screw 109 loosened, the projecting direction of the arm 106 can be changed as shown by the arrow H even in a horizontal plane. The other arm 106B connected at one end with this arm 106A through the articulation 105 can be varied and adjusted in the angle $\theta$ in the horizontal plane between the arms 106A and 106B. That is to say, as shown by the arrow $H_2$, the projecting direction of the other arm 106B can be changed with respect to arm 106A.

The holding part 108 formed at the tip of this arm 106B is formed by fitting the arm 106B at the tip into a C-ring-like receiving frame 110 so that the endoscope 107 may be held rotatably as shown by the arrow A around the axis of the arm 106B.

This endoscope 107 comprises an elongated insertable part 111 made insertable into the mouth cavity of the patient, a large width operating part 112 connected to the rear end of this insertable part 111 and such peripheral apparatus part as a video processor (not illustrated) connected through a universal cord 114 by fitting a connector 113 to this operating part 112. A curving operation knob 115 is provided to project on this operating part 112 so that, by rotating this knob 115, a curvable part provided near the tip of the insertable part 111 may be curved.

Now, as shown in FIG. 10, a break preventing part 117 shaped to be conical, of rubber or the like, is formed on the fitting base part of the operating part 112 that connects with the rear end of the insertable part 111. As shown in FIGS. 9 and 10, a ring-like attachment 118 having a flange 118a formed at the upper end is fitted on the outer periphery of part 117. The C-ring-like receiving frame 110 can be externally fitted to the periphery of the attachment 118. The endoscope 107 fitted with this attachment 118 is rotatable as shown by the arrow B within the receiving frame 110 and can rotatably displace the operating part 112.

By the way, this receiving frame 110 is made C-ring-like by incising a ring. The width of this incision 110a is made somewhat larger than the outside diameter of the insertable part 111. Therefore, by passing the insertable part 111 through this incision 110a, for example, as in FIG. 9, the endoscope 107 can be held by simply holding the attachment 118 with the receiving frame 110. Also, the insertable part can be simply removed through the incision 110a.

Now, the receiving frame 110 is rotatable as shown by the arrow A around the axis of the arm 106B as shown in FIG. 8. However, if the receiving frame 110 rotates in excess, the flange 118a part will contact the receiving frame 110, there will be no regulation of the downward movement and the endoscope 107 will be likely to drop. Therefore, in order to prevent such drop, as shown in FIG. 11, a rotation regulating means (regulating the rotation over a certain angle range) is formed.

That is to say, pins 121a and 121b are provided to project near the tip of the arm 106B and, on the other hand, a pin 122 is provided to project in the axial direction of the arm 106B on the receiving frame 110 side. Therefore, in FIG. 11, if the receiving frame 110 side is rotated and inclined as shown, for example, by the reference numeral A1 with respect to the arm 106B, the pin 121b will contact the pin 122 to limit the angle of inclination, and therefore the endoscope 107 can be prevented from dropping away.

By the way, the above mentioned attachment 118 is of a metal or a plastic material. The break preventing part 117 is weakly pressed into this attachment 118 so that the attachment 118 is fixed to the break preventing part 117.

The operation of the thus formed eighth embodiment shall be explained in the following.

By passing the insertable part 111 through the incision 110a of the receiving frame 110 in the eighth embodiment as shown in FIG. 9, the flange part 118a of the attachment 118 can be supported by the receiving frame 110 to hold the endoscope 107.

By adjusting the arm receiver 104 fixing height and the arm 106A projecting direction so that the endoscope 107 may be in a desired position with respect to the mouth of the patient, the endoscope 107 is kept as held in the eighth embodiment. This state is as shown, for example, in FIG. 8. Even in case it is necessary to twist the operating part 112, it can be simply twisted. Also, the position of the operating part 112 can be easily changed by parallelly progressively displacing the operating part 112 by changing the direction of the arm 106B with the articulation 105 or by changing the arm receiving part 104 fixing height with the fixing screw 109. Also, for example, the operating part 112 can be quickly twisted by the operator. The structure is simple and is adjusted with little trouble. There is no danger to the patient that might be caused by misoperation or accidental running. According to the thus functioning eighth embodiment, the endoscope 107 can be held by the holding part 108 during the operation and therefore the operator is not fatigued.

Also, the endoscope does not drop and is therefore safe to the operator and patient.

Figure 12:
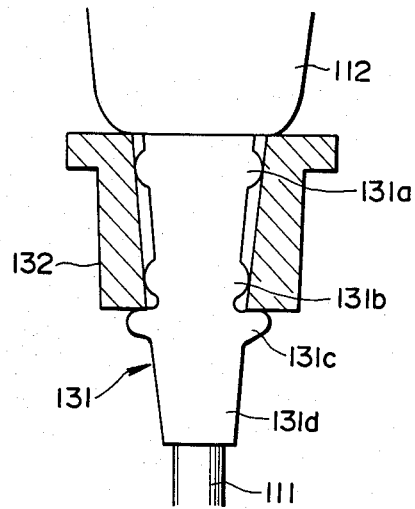
FIG. 12 is a sectioned view showing an attachment fitted to a breaking stopping part different from that of the first embodiment.

FIG. 12 shows other embodiments of the break preventing part and attachment. Small projections 131a and 131b locally expanded in the diameter are formed in break preventing part 131 formed in the fitting base part of the operating part 112 so as to be locally pressed into contact with an attachment which is pressed in. A removal stopping projection 131c is provided to prevent the removal of the attachment 132 by contacting the lower end of the attachment. A second break preventing part 131d for preventing buckling is formed below this projection 131c.

By such formation, the pressing points in the attachment 132 are localized to avoid damaging the flexible tube of the insertable part.

Figure 13:
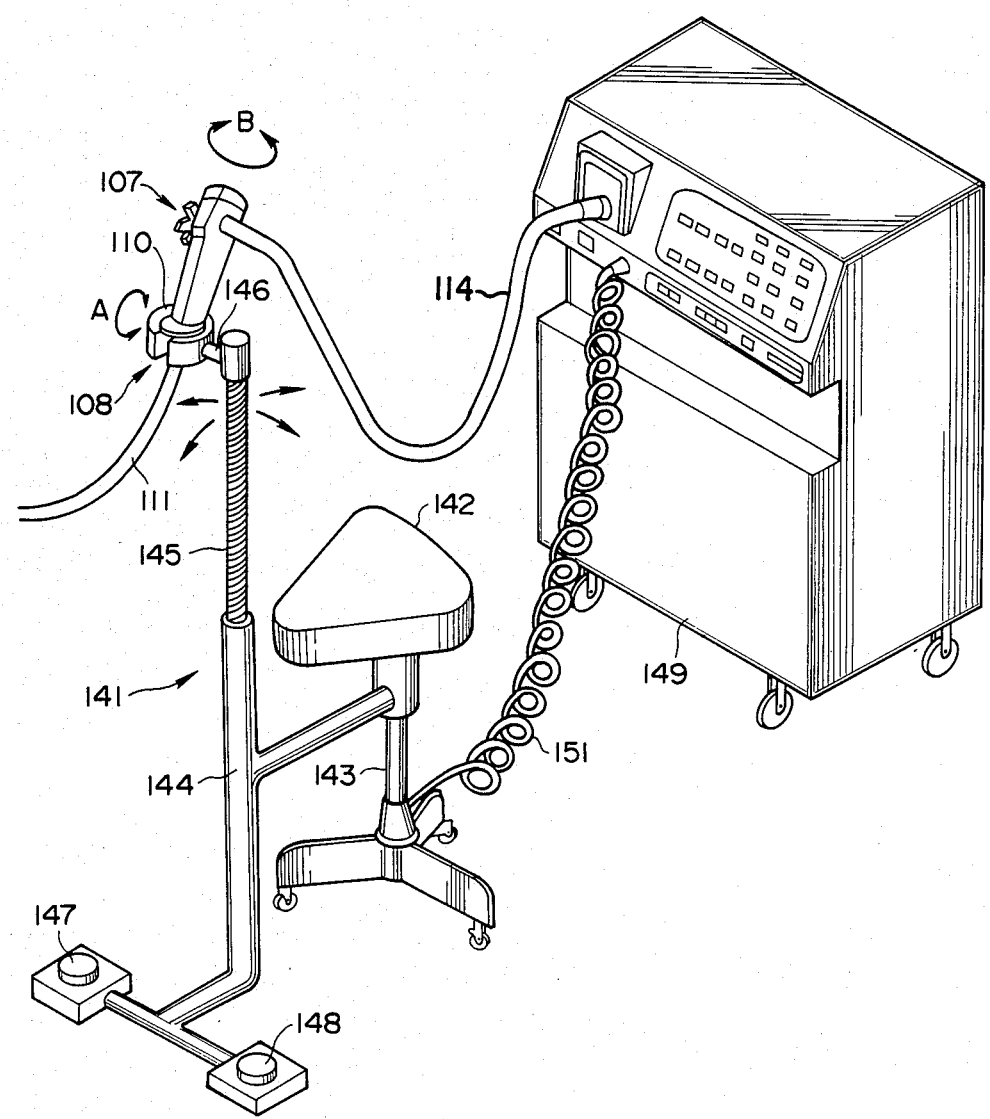
FIG. 13 is a schematic perspective view showing the ninth embodiment of the present invention.

FIG. 13 shows the ninth embodiment of the present invention.

In an endoscope holding apparatus 141 of this embodiment, an arm 144 is projected upward on the forward side of a saddle from a supporting pillar 143 of a chair 142 on which the operator is to sit and a curvable flexible arm 145 is fitted on the top side of this arm 144. The holding part 108 used in the embodiment (the holding part 131 in FIG. 12) is fitted to the tip of this flexible arm 145 through a short arm 146 so as to be able to hold the endoscope 107.

The above mentioned flexible arm 145 is formed of a flexible spiral tube or the like and is bendable in any direction as shown by the arrows. The holding part 108 is rotatable around the axial direction of the short arm 146. Further, the endoscope 107 held by the holding part 108 is rotatable around the center axis of the C-ring-like receiving frame 110 of the holding part 108 as indicated by the arrow B.

Foot switches 147 and 148 are provided on the lower end of the above mentioned supporting pillar 143 and are connected with a video processor 149 through a curled electrical cord 151, for example, extended out of the lower end of the supporting pillar 143. A universal cord 114 extended from the side of the endoscope 107 is connected also to the video processor 149 and the illuminating light from a light source device within the video processor 149 is radiated onto the affected part from the tip of the insertable part through a light guide within the universal cord. An electric signal of an image formed on a light receiving surface by an objective lens (not illustrated) and photoelectrically converted by a solid state imaging device is input to the video processor 149 through the universal cord 114 and is color-displayed on a displaying apparatus. Also, the displayed electric signal can be photographed.

By the way, the connection by this curled cord can be used for the connection by the universal cord of the foot switch, switch box switch, video processor and peripheral apparatus in the other embodiments.

By the way, when the height of the saddle of the chair 142 is made a little lower than the thigh of the operator as standing and the height of the holding part 108 is as high as or a little higher than the navel of the operator as seated on the chair 142, the operator will be able to inspect the object with the same sense as when inspecting it while standing in the conventional example and will be less fatigued.

The operation of the thus formed ninth embodiment is substantially the same as the above mentioned eighth embodiment.

When such switches used frequently by the operator during the operation as, for example, freeze or release switches are arranged in the foot switches 147 and 148, they will be convenient to the operation. If the operator is standing, it will be hard to keep the foot raised to press the foot switch. However, as in the ninth embodiment, the operator can operate the endoscope while sitting on the chair 142 and therefore is not fatigued. Further, the curled cord 151 is used for the switch connecting cable and therefore can be compacted to be small even when the chair 142 approaches the video processor 149. The cord is not likely to be trod by the castor of the chair 142 and the chair 142 is easy to move.

The ninth embodiment has not only substantially the same effects as of the eighth embodiment but also accomplished the following effects.

Even if the operator moves together with the chair 142, the foot switches 147 and 148 and endoscope 107 will move together and will be always in the same positions and therefore the operator will not be fatigued and will find them convenient. As the curled cord 151 is used, it will not be in the way even when the chair 142 approaches the video processor 149.

By the way, the saddle of the above mentioned chair 142 has no back rest so that the operator may easily stand up and sit down and is made narrow so as to be easily held by the thighs.

By the way, the universal cord 114 may be also made a curled cord.

In FIG. 13, even if the holding part 108 holding the endoscope 107 and the arm 144 are not provided and only the foot switches 147 and 148 are provided on the chair 142 on which the operator is to sit, for the foot switches which are hard to use while the operator is standing, the operator need not apply the body weight on the feet while sitting. Therefore, when using the chair 147 there is an effect that the foot switches are easy to use.

Figure 2:
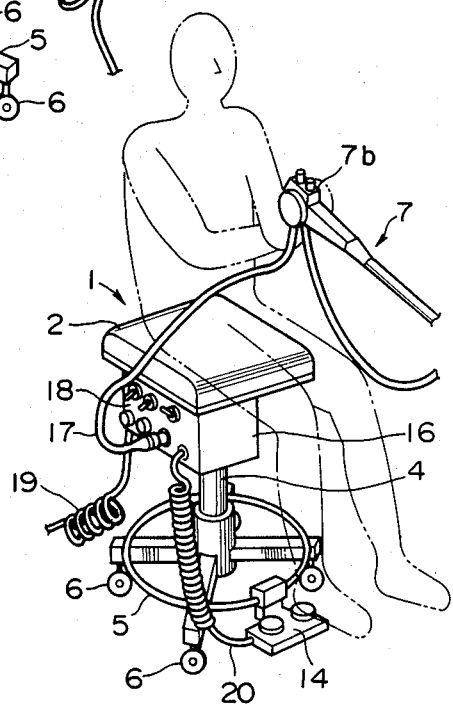
Figure 3:
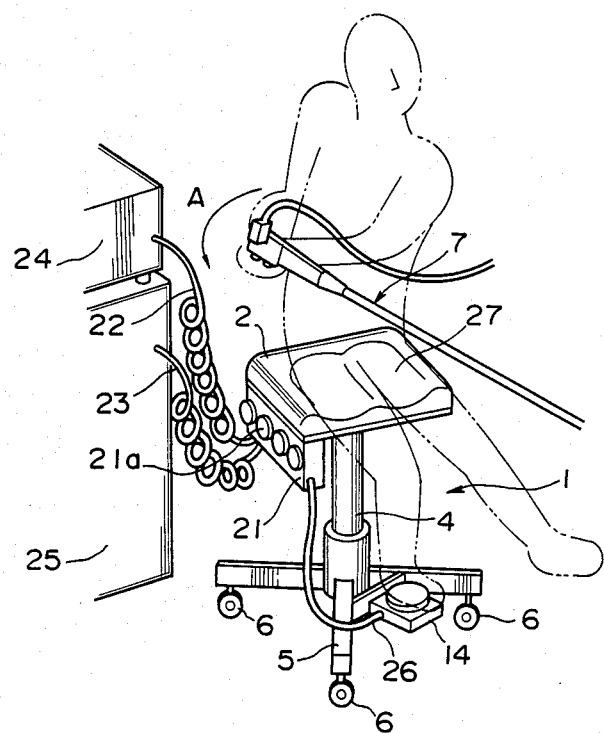

By the way, in this embodiment, such endoscope apparatus as light and current sources may be arranged in the chair 142 as in the respective embodiments shown in FIGS. 1 to 3.

Figure 15:
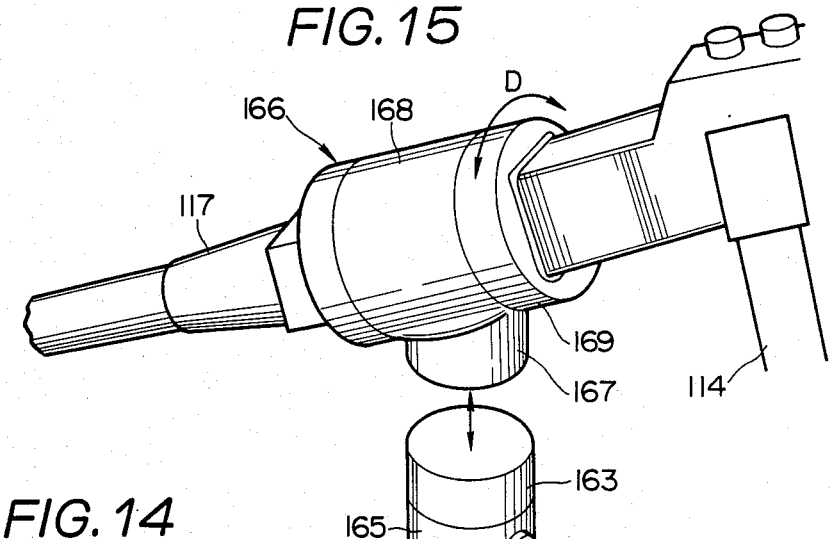
FIG. 15 is a perspective view showing the surroundings of a holding part in the tenth embodiment.
Figure 14:
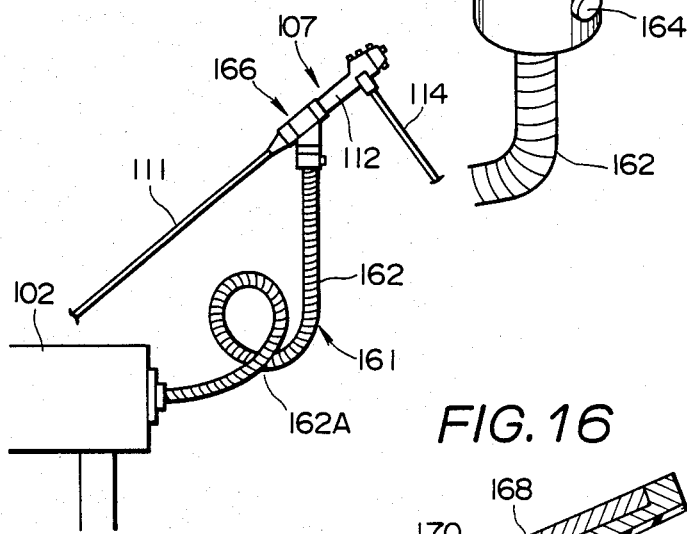
FIG. 14 is a schematic perspective view showing the tenth embodiment of the present invention.

FIG. 14 shows a holding apparatus 161 of the tenth embodiment of the present invention. A flexible arm 162 is fitted to a bed 102 and is provided with a looped part 162 A on the way. An electromagnet 163 as is shown in FIG. 15 is fitted to the tip of the flexible arm 162. A switch 164 of the electromagnet 163 is provided in a receiving part 165 of the electromagnet 163. A holding part 166 for holding the endoscope 107 comprises a receiving member 168 provided with a fitting part 167 to be in close contact with the end surface of the above mentioned electromagnet 163 as shown in FIG. 15 and a rotary frame 169 rotatable fitted to this receiving member 168 as indicated by the arrow D and holding the endoscope 107 inside.

Figure 16:
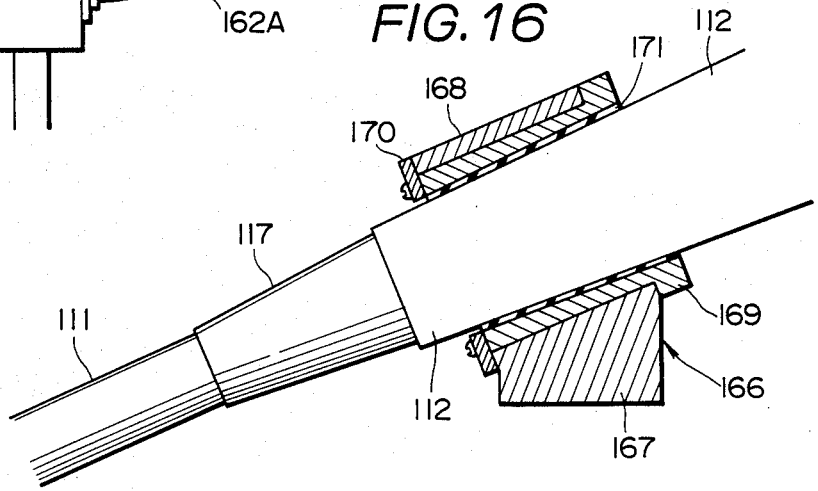
FIG. 16 is a sectioned view showing the holding part in the tenth embodiment.

The above mentioned holding part 166 and flexible arm 162 are removably fitted to the electromagnet 163. A removal preventing frame 170 is integrally fixed to the rotary frame 169 as shown in FIG. 16 so that the rotary frame 168 may not escape out of the receiving member 168. A rubber member 171 is adhered to the inside surface of the rotary frame 169, that is, to the part to be in contact with the endoscope 107 so as to hold the endoscope 107 with friction. By the way, the method of removably fitting the holding part 166 by using the electromagnet 163 can be used not only for the tip of the flexible arm 162 extended out of the bed 102 as in this embodiment but also may be applied to the other embodiments. The electromagnet may be provided on the holding part 166 side instead of the arm 162 side. The part to which the holding part 166 is fitted is not the break preventing part 117 in this embodiment but is a gripping part on the lower side of the operating part 112 as shown in FIG. 16 so as to maintain the break preventing effect.

The operation of this tenth embodiment is the same as of the above mentioned eighth embodiment.

This tenth embodiment has not only the same effects as of the above mentioned eighth embodiment but also the following effects.

As the looped part 162A is provided on the way of the flexible arm 162, the endoscope moves smoothly in all directions.

Now, when the operating part 112 is to be moved in a wide range, it will be likely to exceed the movable range of the flexible arm 162 and the like. In such case, it is desirable to somewhat narrow the movable range of the holding part to compact the holding part. When the movable range is exceeded, the operating part 112 may be removed from the holding part so as to be used as before. In this embodiment, as the removably fitting part is formed by using the electromagnet 162, the operating part 112 need not be removed from holding part 166 when it is fitted or removed.

Figure 17:
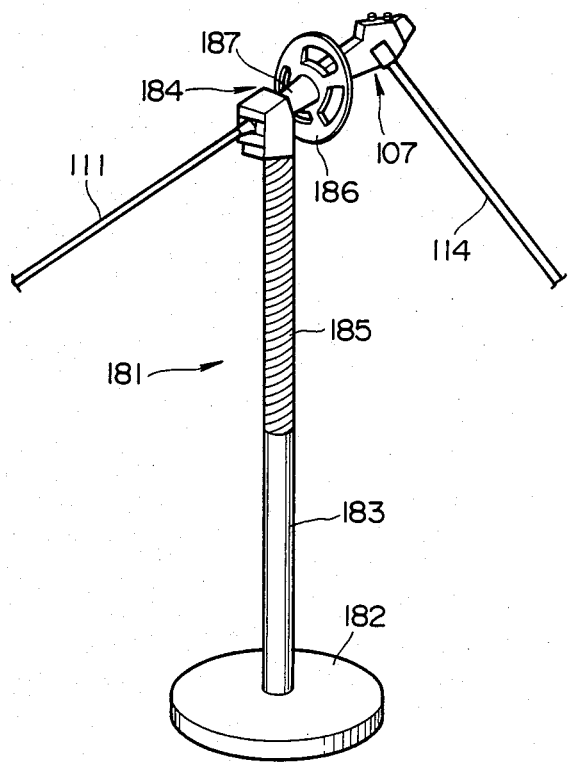
FIG. 17 is a schematic perspective view showing the eleventh embodiment of the present invention.

FIG. 17 shows a holding apparatus 181 of the eleventh embodiment of the present invention.

Figure 18:
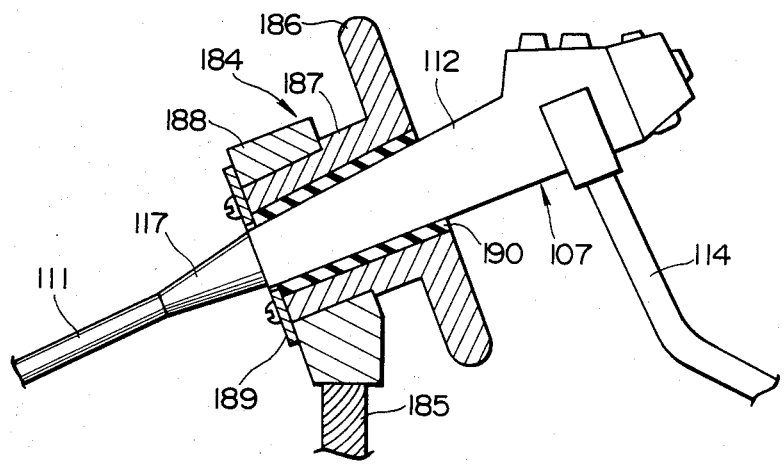
FIG. 18 is a sectioned view showing a holding part in the eleventh embodiment.
Figure 19:
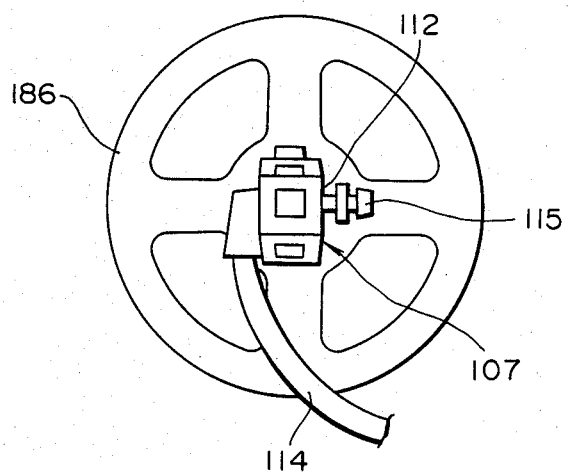
FIG. 19 is an elevation showing a handle part in the eleventh embodiment.

An arm 183 is erected on a stand 182. A holding part 184 of the endoscope 107 is fitted to the upper end of the arm 183. A part of the above mentioned arm 183 is formed of a flexible arm 185. As shown in FIG. 18, a rotary frame 187 holding the endoscope 107 and having a handle part 186 formed thereon is in the holding part 184 and is rotatably fitted in a receiving frame 188. The shape of the handle part 186 of the rotary frame 187 is substantially circular as shown in FIG. 19.

By the way, the reference numeral 189 represents a removal stopper of the handle part 186.

A rubber member 190 is provided on the inside surface of the rotary frame 187 so as to hold the endoscope 107 by friction.

The operation of this embodiment is the same as of the above mentioned eighth embodiment.

This embodiment has not only the same effects as of the above mentioned eighth embodiment but also the following effects.

As the rotary frame 187 holding the endoscope 107 has the handle part 186, the endoscope is easy to rotate and is convenient.

Figure 20:
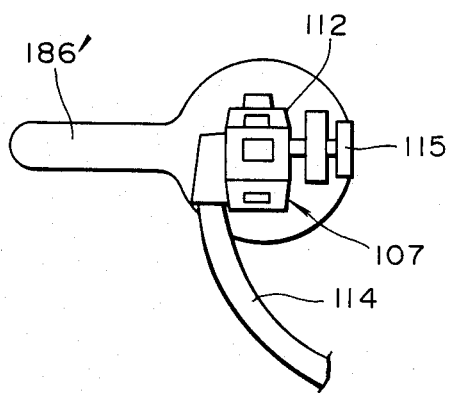
FIG. 20 is an elevation showing an embodiment of a handle part different from that in FIG. 19.

By the way, as shown in FIG. 20, a rotary operating lever 186' may be provided instead of the handle part 186 shown in FIG. 19.

The rotary mechanism having the above mentioned handle part 186 or lever part 186' can be applied also to the other embodiments.

Figure 21:
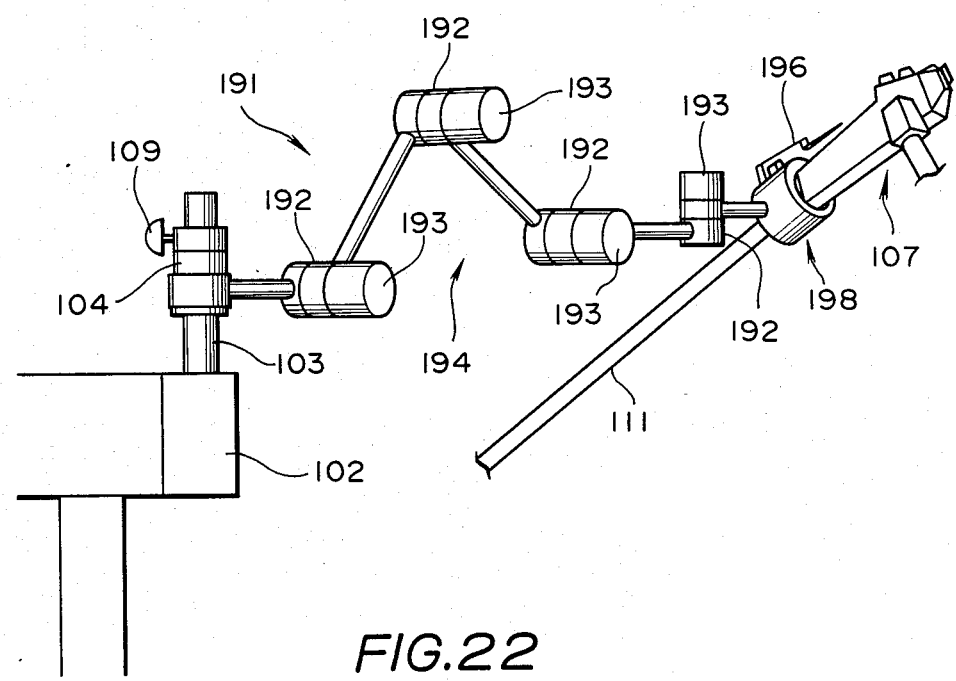
FIG. 21 is a schematic perspective view showing the twelfth embodiment of the present invention.
Figure 22:
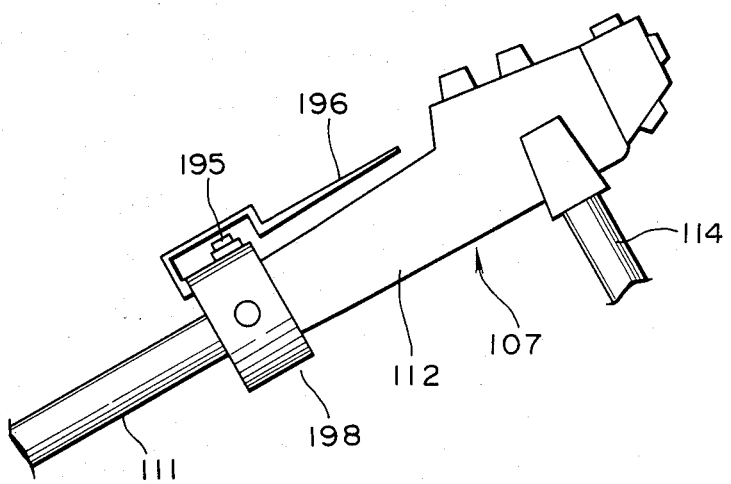
FIG. 22 is a side view showing a holding part in the thirteenth embodiment.

FIG. 21 shows a holding apparatus 191 of the twelfth embodiment of the present invention. In this embodiment, a plurality of articulating parts 192 are provided and electromagnetic clutches 193 are provided on the respective articulating parts 192 to form a multi-articulation arm 194. This multi-articulation arm 194 is fixed at one end to the arm receiver 104 fitted to the supporting pillar 103 erected on the bed 102 and is fixed to the supporting pillar 103 with the fixing screw 109. A holding part 198 is provided at the other end of this multi-articulation arm 194 and is provided with an operating switch 195 of the above mentioned electromagnetic clutches 193. When this operating switch 195 is pushed, the electromagnetic clutches 193 will loosen and the arms in front and rear of them will become free to rotate.

When this operating switch 195 is not pushed, the respective electromagnetic switches 193 will be tight and the arms in front and rear of them will be fixed. An auxiliary lever 196 is provided on the holding part 198 so that, when the operator only grips the operating part 112 of the endoscope, the operating switch 195 will be pushed. By the way, this mechanism may be used also for a mono-articulation arm.

This arm fixing mechanism by the electromagnetic clutches 193 may be used for multi-articulation arms or mono-articulation arms provided not only for the multi-articulation arm coming out of the bed 2 but also for the chair, peripheral apparatus, floor and wall.

According to the above mentioned twelfth embodiment, when the operating part 112 is gripped to move the endoscope 107, the switch 195 will be engaged, the respective articulations of the arm will loosen and the endoscope 107 will be able to be freely moved.

When the endoscope 107 is positioned and is released from the grip, the operating switch 195 will be disengaged, the articulations of the arm will be fixed and the endoscope will be able to be held. The other operations are the same as of the eighth embodiment. This embodiment has the effects of the above mentioned eighth embodiment, is easy to swing and hold the endoscope 107 and is convenient to the operation.

Figure 23:
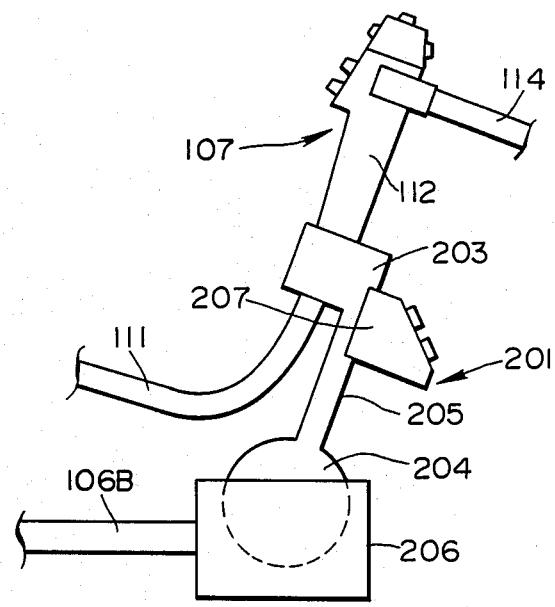
FIG. 23 is a schematic side view showing the fourteenth embodiment of the present invention.
Figure 24:
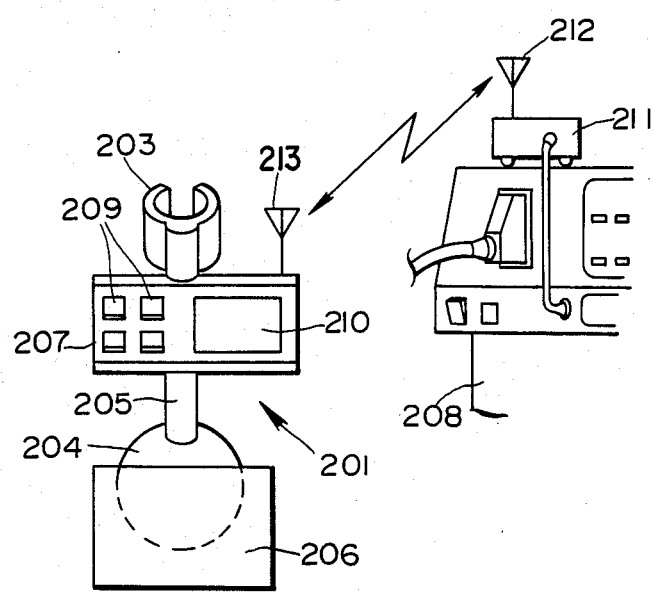
FIG. 24 is an elevation showing a switch box in the fourteenth embodiment.

FIG. 23 shows a holding part 201 of a holding apparatus of the fourteenth embodiment of the present invention. In this embodiment, the holding part 201 is different from those of the other embodiments and comprises an arm 205 having an endoscope fitting part 203 at one end and having a spherical part 204 at the other end and an arm receiver 206 receiving the spherical part 204 of the arm 205. The spherical part 204 and arm receiver 206 are rotatably fitted with each other. A switch box 207 is provided on the way of the arm 205. Switches 209 for operating such peripheral apparatus 208 (See FIG. 24) as a video processor and a monitor 210 are incorporated in the switch box 207. In the case of this embodiment, information is exchanged by wireless between the switch box 207 and peripheral apparatus 208. Therefore, a transmitter-receiver 211 is separately provided for the peripheral apparatus 208. A transmitter-receiver is built in the switch box 207. By the way, the reference numerals 212 and 213 represent antennae for the respective transmitter-receivers. The switches 209 and monitor 210 in the switch box 207 in this embodiment may be separate and may be fitted in the holding part, arm part or articulating part in this and other embodiments. By the way, the fitting part 203 is formed of such C-ring-like receiving frame as is shown in FIG. 8 secured to the arm 205. The arm receiver 206 is fitted to the tip of the arm 106B, for example, in FIG. 8.

According to this embodiment, when the arm receiver 206 is fixed, if the endoscope 107 is moved, as the fulcrum (the spherical part 204 of the arm 205) is below the gripping part by the hand, the endoscope 107 will move to fall. The other operations are the same as in the eighth embodiment.

In this embodiment, there are the same effects as of the eighth embodiment and, when the endoscope 107 is moved or inclined as held, it will move to fall naturally and therefore will have no sense of difference.

Figure 25:
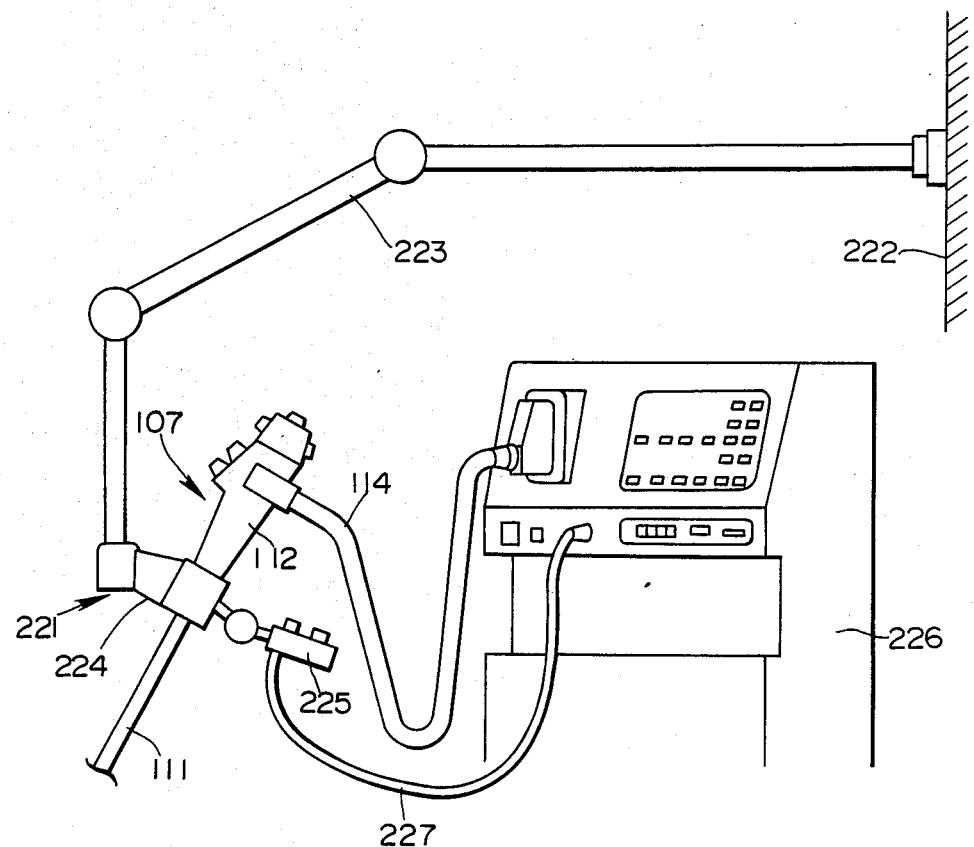
FIG. 25 is a schematic side view showing the fifteenth embodiment.

FIG. 25 shows a holding apparatus 221 of the fifteenth embodiment of the present invention. A multi-articulation arm 223 is fitted on the base to a wall 222 of a building and a holding part 224 for the endoscope 107 is provided at the tip of the arm 223. A switch box 225 is provided on the holding part 224 and is connected with such peripheral apparatus 226 as a video processor through a cable 227 in the case of this embodiment.

The operation of this embodiment is the same as that of the above mentioned eighth embodiment. In this embodiment, such holding part as the supporting pillar of the holding apparatus 221 holding the endoscope 107 is not around the feet of the operator and therefore is not in the way to the operator. Otherwise, it has the same effect as of the above mentioned eighth embodiment.

Figure 26:
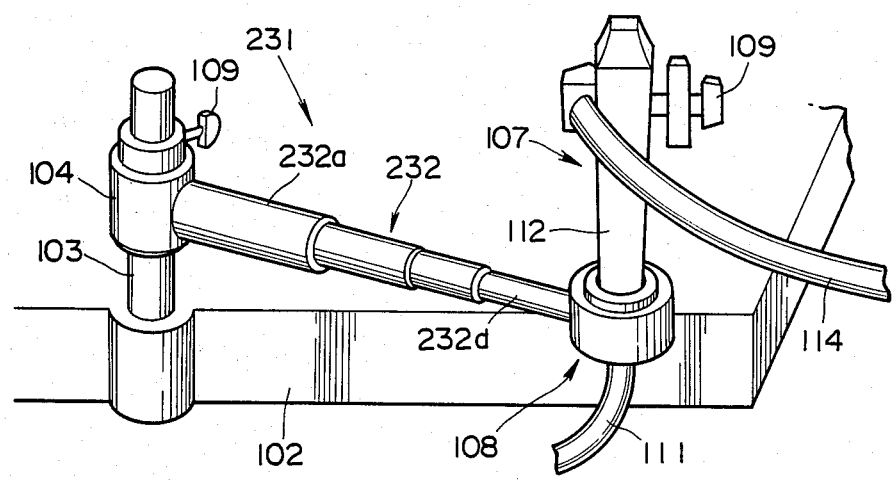
FIG. 26 is a schematic perspective view showing the sixteenth embodiment.

FIG. 26 shows a holding apparatus 231 of the sixteenth embodiment of the present invention.

Figure 27:
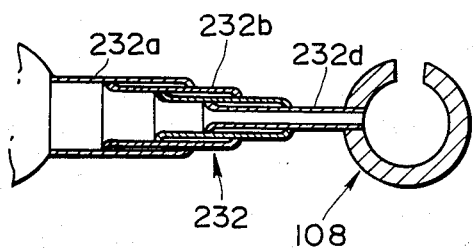
FIG. 27 is a sectioned view showing a retractable arm in the sixteenth embodiment of the present invention.

In this embodiment, a telescopic arm 232 formed by slidably fitting pipes 223a, 232b, etc., each progressively smaller in diameter as shown in FIG. 27 is used in place of the arms 106A and 106B in the eighth embodiment. The pipe 232a of the largest diameter is secured on the base to the arm receiver 104. A holding part 108 is formed at the tip of the pipe 232d of the smallest diameter. Otherwise, the formation is the same as that of the above mentioned eighth embodiment. The operations and effects are also substantially the same as those of the above mentioned eighth embodiment.

Figure 28:
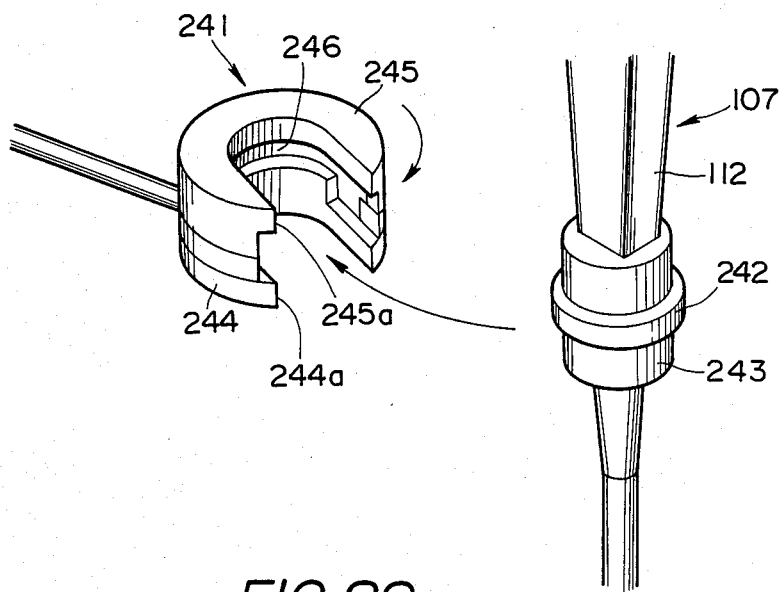
FIG. 28 is a perspective view showing a holding part of the seventeenth embodiment of the present invention.

FIG. 28 shows the seventeenth embodiment of the holding part in the present invention.

Figure 29:
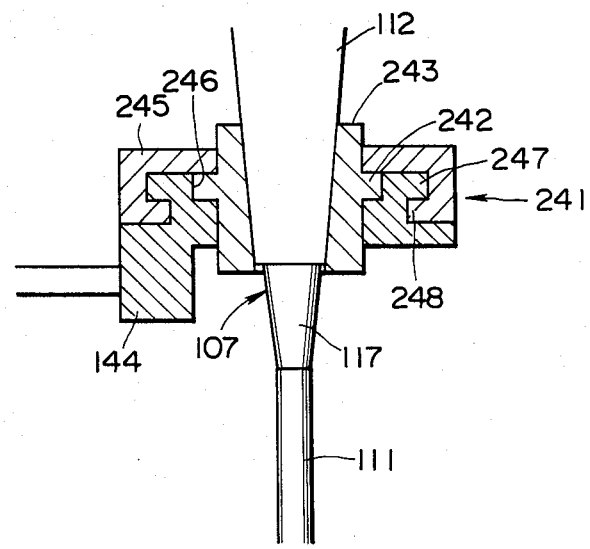
FIG. 29 is a sectioned view showing the structure of the holding part as holding an endoscope.

In this holding part 241, a cylindrical attachment 243 provided with a projecting annular part 242 on a part of the outer periphery is integrally fixed to the operating part 112 of the endoscope 107. On the other hand, the holding part 241 comprises a fixed frame 244 and rotary frame 245. These two frames are combined with each other to form a groove 246 in which the annular part 242 of the above mentioned attachment 243 is to be fitted. The fixed frame 244 and rotary frame 245 are rotatably fitted with each other and are formed with respective pawls 247 and 248 so as to positively engage with each other as shown in FIG. 29. Openings 244a and 245a are provided respectively in the fixed frame 244 and rotary frame 245. The attachment 243 is put in and out by making both openings 244a and 245a coincide with each other. When the endoscope 107 is to be held, the attachment 243 is put into the holding part 241, the rotary frame 245 is then rotated by more than 90 degrees but les than 180 degrees so that the attachment may not be removed. In this state, the attachment 243 is rotatable with respect to the holding part 241.

In this embodiment, when the endoscope 107 is held, the endoscope 107 and holding part 241 will be rotatable and, even if the endoscope 107 is pulled and pushed in any direction, it will not be removed.

As an effect of this embodiment, when the endoscope 107 is fitted, it will not be removed from the holding part 241 and will be therefore safe and convenient. By only making the openings of the rotary frame 245 and fixed frame 244 coincide with each other, the endoscope 107 can be removed.

By the way, the holding mechanism of this holding part 241 can be applied to the above described embodiments.

FIGS. 30 to 36 relate to an embodiment wherein the chair of the present invention and the bed for the patient are operatively connected with each other.

Figure 30:
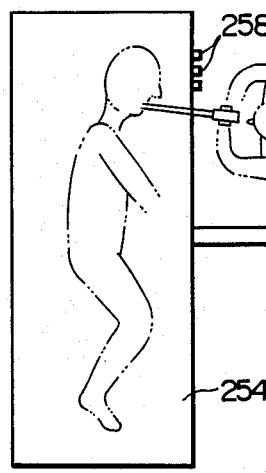
FIG. 30 is a schematic plan view showing the eighteenth embodiment of an auxiliary apparatus of the present invention wherein a chair and bed are operatively connected with each other.
Figure 31:
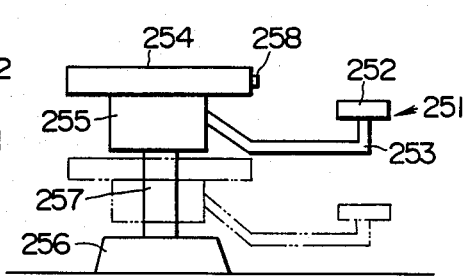
FIG. 31 is a side view of FIG. 30.

FIGS. 30 and 31 show the eighteenth embodiment of the present invention. In this embodiment, a chair 251 comprises a seat part 252 and a frame 253 and is fitted to a bed 254 through the frame 253 so as to vertically move in response to the vertical movement of the bed 254. The above mentioned bed 254 is mounted on a bed receiver 255 fixed to a rod 257 moved vertically by such elevating apparatus as, for example, an oil pressure apparatus or a motor. An operating switch 258 for vertically moving the above mentioned bed 254 is provided, for example, on the side part of the bed 254.

A vertically movable bed for the patient already exists but the chair is adjustable in height and is fixed to the bed. Now, when the patient is to mount or dismount the bed, the bed had better be in a low position but, at the time of the inspection, the mouth of the patient had better be in a position easy to be reached by the hand of the of the operator. Therefore, it is desirable to make the chair low. However, if the chair is too low, the patient will be fatigued very much in sitting down and standing up. On the other hand, if the chair is made high in advance, it will be in the way at the time no inspection elevating apparatus.

Therefore, if the bed 254 is made low at the time of no inspection by the above mentioned formation, it will be easy for the patient to mount and dismount the bed and also, if the bed is low, the chair will also become low as operatively connected with the bed and will not be in the way to the operator. When the bed 254 is elevated at the time of the inspection, the mouth of the patient will be in the hand position of the operator and will be easy to inspect. As the chair 251 will be also high, the operator will find it easy to sit on the chair.

By the way, the seat part 252 may be either rotatable or fixed with respect to the frame 253. It is preferable that the chair 251 and bed 254 can be locked in any vertical position.

Figure 32:
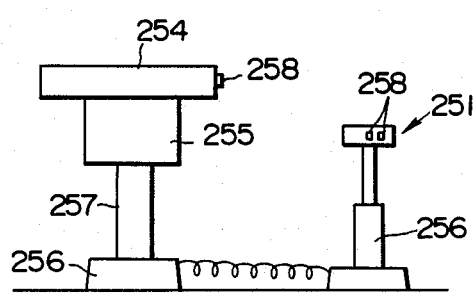
FIG. 32 is a schematic side view showing the nineteenth embodiment of the present invention.

FIG. 32 shows the nineteenth embodiment of the present invention wherein the chair 251 and bed 254 are separate from each other, elevating apparatus 257 are arranged respectively in them and operating switches 258 are provided respectively in them. By the way, the elevating apparatus 256 may be electrically connected with each other as required so as to synchronize the vertical movements of both.

Figure 33:
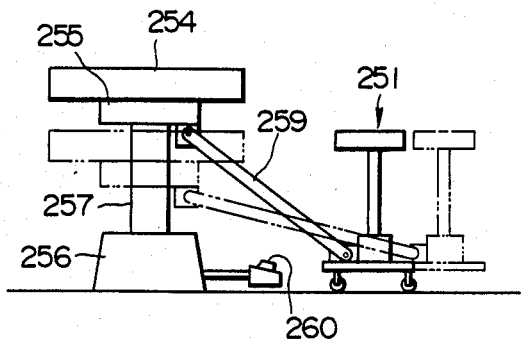
FIG. 33 is a schematic side view showing the twentieth embodiment of the present invention.
Figure 34:
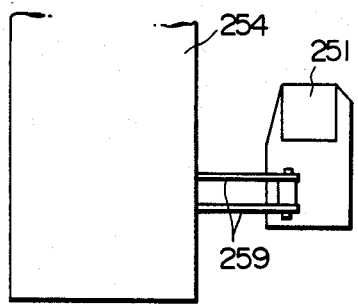
FIG. 34 is a plan view of FIG. 33.

FIGS. 33 and 34 show the twentieth embodiment of the present invention wherein the chair 251 is connected to the vertically movable bed 254 through arms 259 which are rotatably borne at both ends connected respectively with the bed 254 and chair 251 so that, when the bed 254 rises through these arms 259, the chair 251 will approach the bed 254 and, when the bed 254 descends, the chair 251 will move away from the bed. Therefore, at the time of no inspection, when the patient mounts or dismounts the bed 254, the chair 251 will be in a separate position so that the bed may be easy to mount or dismount. By the way, a foot switch 260 is provided as an operating switch.

Figure 35:
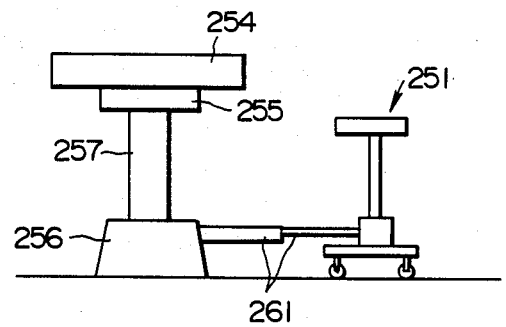
FIG. 35 is a schematic side view showing the twenty-first embodiment of the present invention.

FIG. 35 shows the twenty-first embodiment of the present invention wherein the bed 254 and chair 251 are connected with each other through a retractable connecting member 261 instead of the arm in the twentieth embodiment. In this embodiment, the ratio of the vertical movement of the bed 254 to the approach or separation of the chair 251 is not always 1:1 but can be freely set.

Figure 36:
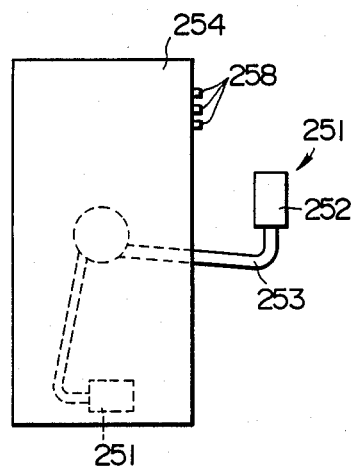
FIG. 36 is a schematic side view showing the twenty-second embodiment of the present invention.

FIG. 36 shows the twenty-second embodiment of the present invention. In this embodiment, in addition to the formation of the above mentioned embodiment in FIGS. 30 and 31, the chair 251 is rotatably borne by the bed 254 through the frame 253 so that, at the time of no inspection, the chair 251 will descend and will retreat under the bed 254 but, at the time of the inspection, the chair 251 will rise and will come out to a proper position.

In the above mentioned respective embodiments shown in FIGS. 30 to 36, the formations in FIGS. 1 to 4 and the holding apparatus in FIG. 13 are added to the chair as required.

In the present invention, it is apparent that working modes different in a wide range can be formed on the basis of this invention without deviating from the spirit and scope of the invention. This invention is not restricted by its specific working modes except being limited by the appended claims.

What is claimed is:

1. An endoscope chair apparatus comprising:
an endoscope having an operating part, an insertable part for insertion into a patient, and a universal cord for connecting the endoscope to an endoscope peripheral apparatus;
an endoscope peripheral apparatus directly connected to said endoscope by said universal cord; and
a chair remote from said endoscope peripheral apparatus and operatively connected by only an electrical cord to said endoscope peripheral apparatus, said chair having mounted thereon at least an operating switch for said endoscope peripheral apparatus, said switch being connected to said electrical cord.

2. An endoscope chair apparatus as recited in claim 1, wherein said endoscope peripheral apparatus includes at least one of a current and light source for said endoscope, a video processor, a recording apparatus, a laser cauterizing apparatus and a high frequency current source connected to said endoscope operating part, and said operating switch controls said peripheral apparatus.

3. An endoscope chair apparatus as recited in claim 2, wherein said operating switch is a foot switch provided in a position to be operated by an operator while sitting on said chair.

4. An endoscope chair apparatus as recited in claim 1, wherein said chair is operatively connected to a bed for a patient for movement in accordance with vertical movement of said bed.

5. An endoscope chair apparatus as recited in claim 4, wherein said chair moves vertically with vertical movement of said bed.

6. An endoscope chair apparatus as recited in claim 5, wherein said chair is pivotally supported with respect to the bed to move between positions under and beside the bed.

7. An endoscope chair apparatus as recited in claim 1, further including endoscope holding apparatus supportively connected to said chair.

8. An endoscope chair apparatus as recited in claim 7, wherein said chair is connected to a bed for a patient and said endoscope holding apparatus is mounted on said bed.

9. An endoscope chair apparatus as recited in claim 7, wherein said endoscope holding apparatus includes a holding part having a receiving frame for removably receiving and supporting said endoscope, said holding part being rotatable and positionable with said endoscope received therein so as to support and retain said endoscope in a position to which said endoscope is moved by an operator when said insertable part is inserted in a patient.

10. An endoscope chair apparatus as recited in claim 9 wherein said endoscope, removed from said holding apparatus and held by said operator, is without direct connection to said chair such that said chair is movable by said operator to conveniently position said operating switch mounted thereon for operation of said remote endoscope peripheral apparatus by said operator without affecting a position of said endoscope by said chair movement.

11. A endoscope apparatus as recited in claim 1, wherein said chair is mobile with respect to said peripheral apparatus.

12. An endoscope chair apparatus as recited in claim 11, wherein said endoscope peripheral apparatus also is mobile.

* * * * *